US012727910B2

(12) United States Patent
Aliakbari et al.

(10) Patent No.: US 12,727,910 B2
(45) Date of Patent: Sep. 8, 2026

(54) WEARABLE ULTRASOUND

(71) Applicant: FUJIFILM SONOSITE, INC., Bothell, WA (US)

(72) Inventors: Saeed Aliakbari, Snohomish, WA (US); Andrew Lundberg, Seattle, WA (US); Craig Chamberlain, Seattle, WA (US); Keith Williams, Bothell, WA (US); Thomas Endres, Bothell, WA (US)

(73) Assignee: FUJIFILM SONOSITE, INC., Bothell, WA (US)

(*) Notice: Subject to any disclaimer, the term of this patent is extended or adjusted under 35 U.S.C. 154(b) by 0 days.

(21) Appl. No.: 18/132,737

(22) Filed: Apr. 10, 2023

(65) Prior Publication Data

US 2024/0335215 A1 Oct. 10, 2024

(51) Int. Cl.

| | |
|---|---|
| ***A61B 17/34*** | (2006.01) |
| ***A61B 8/00*** | (2006.01) |
| ***A61B 8/08*** | (2006.01) |

(52) U.S. Cl.

CPC .......... *A61B 17/3403* (2013.01); *A61B 8/085* (2013.01); *A61B 8/4427* (2013.01); *A61B 2017/3413* (2013.01)

(58) Field of Classification Search

CPC ... A61B 17/3403; A61B 8/085; A61B 8/4427; A61B 2017/3413

See application file for complete search history.

(56) References Cited

U.S. PATENT DOCUMENTS

| | | | | |
|---|---|---|---|---|
| 10,973,584 B2 * | 4/2021 | Grunwald | .............. | A61B 34/20 |
| 2007/0038100 A1 * | 2/2007 | Nita | .................. | A61M 37/0092 600/439 |
| 2008/0004904 A1 * | 1/2008 | Tran | ....................... | G16H 40/67 340/286.07 |
| 2011/0238107 A1 * | 9/2011 | Raheman | ............... | A61B 5/412 606/202 |
| 2016/0192902 A1 * | 7/2016 | Werneth | ............... | A61B 5/4836 600/374 |
| 2018/0177486 A1 * | 6/2018 | Gifford, III | .............. | A61B 8/12 |
| 2019/0231317 A1 * | 8/2019 | Anthony | ................ | A61B 8/429 |
| 2019/0269381 A1 * | 9/2019 | Masuda | ................. | G16H 50/30 |
| 2020/0214667 A1 * | 7/2020 | Shoudy | ................ | A61B 8/4455 |
| 2020/0359990 A1 * | 11/2020 | Poland | ................... | A61B 8/463 |
| 2021/0169417 A1 * | 6/2021 | Burton | ................. | A61B 5/4857 |
| 2023/0099288 A1 * | 3/2023 | Wang | .................... | B06B 1/0625 345/156 |
| 2023/0149746 A1 * | 5/2023 | Peters | ...................... | A61N 7/00 601/2 |

(Continued)

*Primary Examiner* — Baisakhi Roy

(74) *Attorney, Agent, or Firm* — Womble Bond Dickinson (US) LLP

(57) ABSTRACT

A wearable ultrasound device and method for using the same are disclosed. In some embodiments, the wearable ultrasound device includes an ultrasound transducer configured to transmit ultrasound signals and receive reflected ultrasound based on the ultrasound signals and a fastener configured to secure the wearable ultrasound device proximate to a procedure site. The wearable ultrasound device can also include a processor configured to generate, based on the reflected ultrasound, patient data and a display device implemented to display a visual representation of the patient data.

18 Claims, 10 Drawing Sheets

(56) References Cited

U.S. PATENT DOCUMENTS

| | | | | |
|---|---|---|---|---|
| 2023/0310808 | A1* | 10/2023 | Jansson | A61M 25/02<br>604/179 |
| 2024/0115202 | A1* | 4/2024 | Tran | A61B 5/002 |
| 2024/0164648 | A1* | 5/2024 | Tse | A61B 5/0059 |
| 2024/0181277 | A1* | 6/2024 | Peters | A61N 7/00 |
| 2024/0245387 | A1* | 7/2024 | McGrath | A61B 8/06 |
| 2026/0014395 | A1* | 1/2026 | Peters | A61N 7/00 |

* cited by examiner

802

START

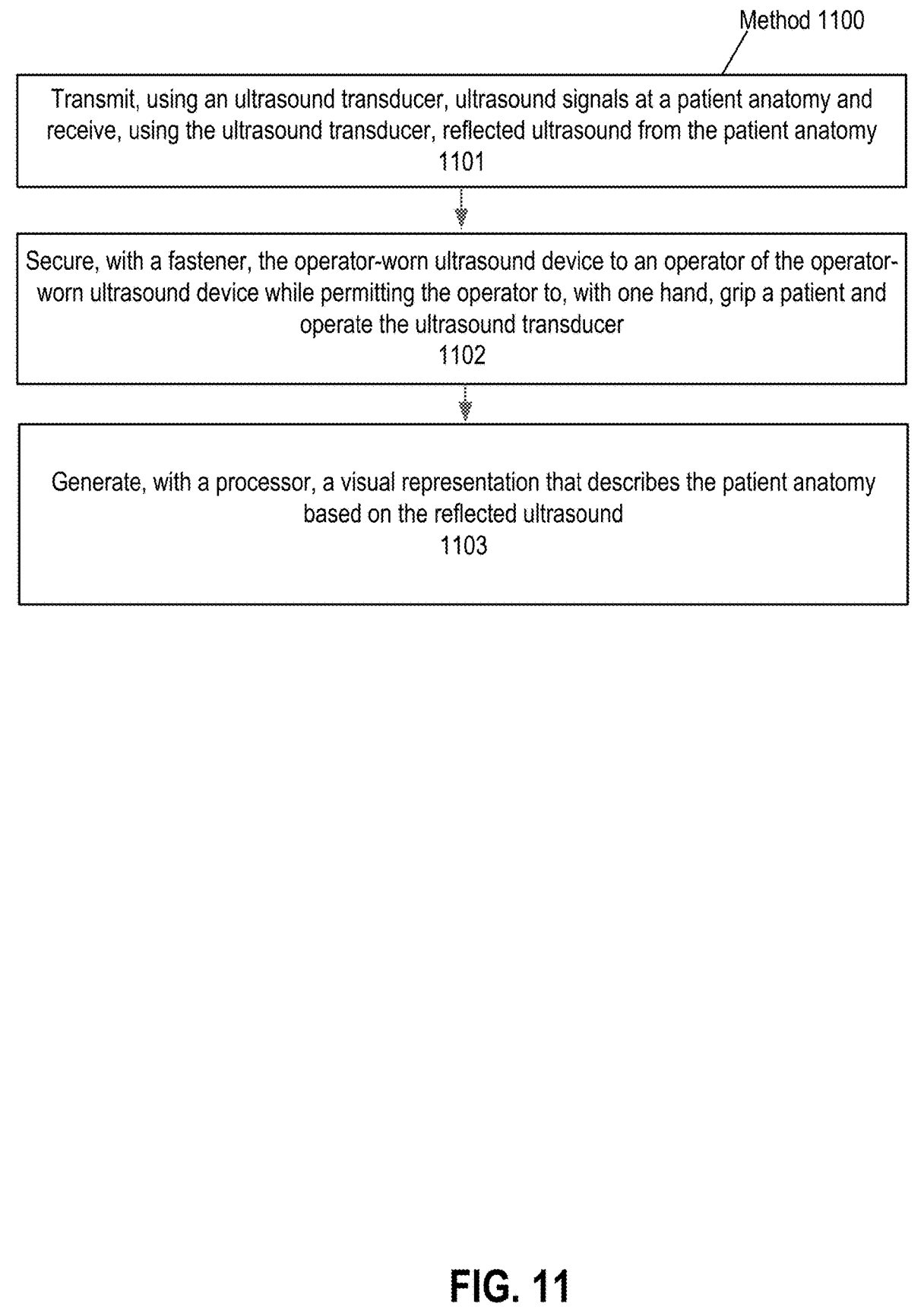

Method 1100

Transmit, using an ultrasound transducer, ultrasound signals at a patient anatomy and receive, using the ultrasound transducer, reflected ultrasound from the patient anatomy
1101

Secure, with a fastener, the operator-worn ultrasound device to an operator of the operator-worn ultrasound device while permitting the operator to, with one hand, grip a patient and operate the ultrasound transducer
1102

Generate, with a processor, a visual representation that describes the patient anatomy based on the reflected ultrasound
1103

FIG. 11

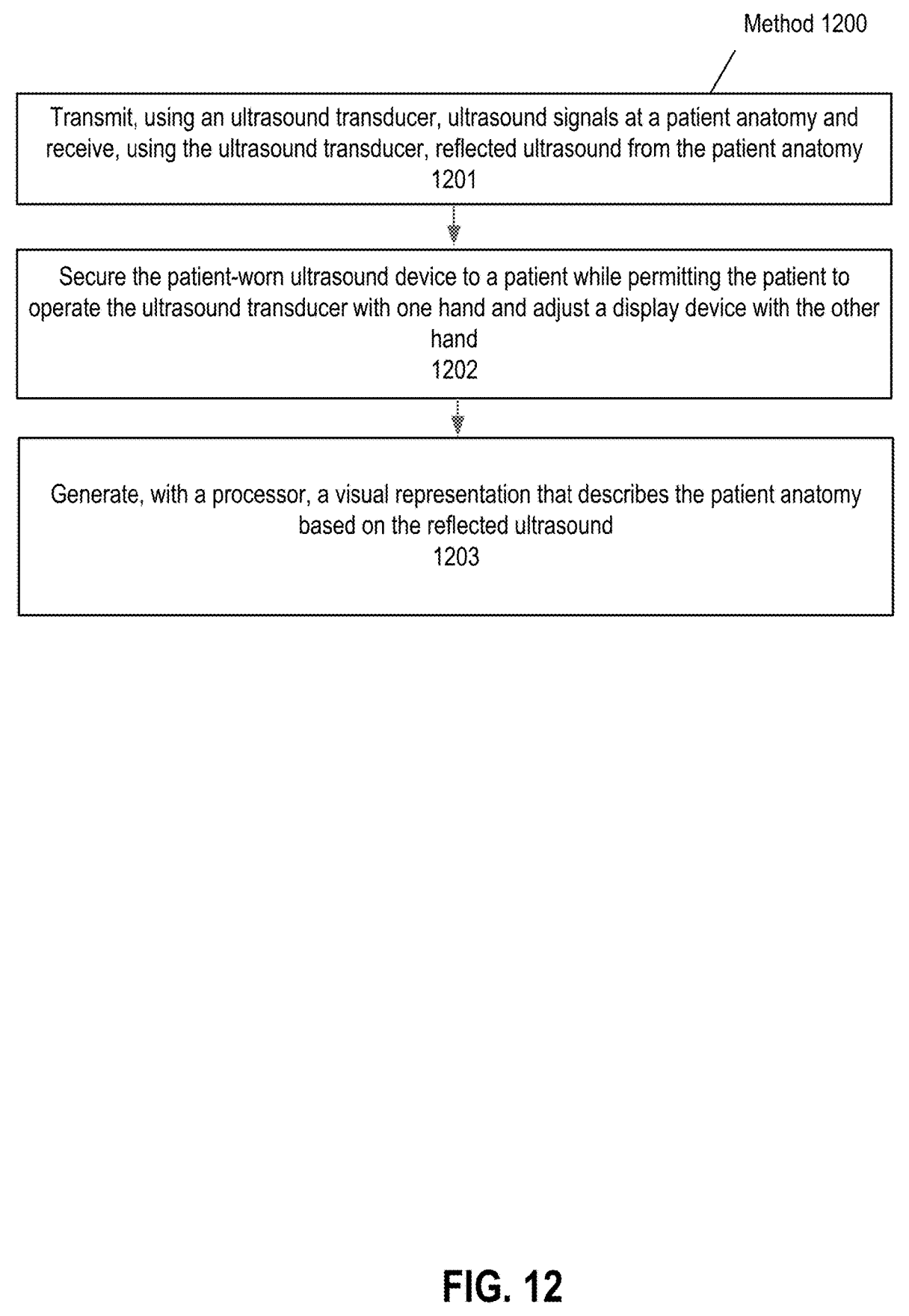

Method 1200

Transmit, using an ultrasound transducer, ultrasound signals at a patient anatomy and receive, using the ultrasound transducer, reflected ultrasound from the patient anatomy
1201

Secure the patient-worn ultrasound device to a patient while permitting the patient to operate the ultrasound transducer with one hand and adjust a display device with the other hand
1202

Generate, with a processor, a visual representation that describes the patient anatomy based on the reflected ultrasound
1203

FIG. 12

WEARABLE ULTRASOUND

FIELD

Embodiments disclosed herein relate to ultrasound systems. More specifically, embodiments disclosed herein relate to ultrasound systems that include an ultrasound device that can be worn by an individual (e.g., an operator, a patient, etc.).

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and can provide immediate imaging results, ultrasound systems are used ubiquitously for various procedures. One example of an ultrasound-assisted procedure is vascular access, such as to guide the insertion of a needle into a vein. However, it is difficult or impossible for a sole ultrasound operator to perform this procedure. For instance, the operator generally needs three hands: one to hold the ultrasound transducer, one to hold and/or adjust the display device (e.g., ultrasound machine), and one to hold and insert the needle. Consequently, multiple operators usually contribute to the procedure. However, the point of care location, such as an emergency room, is usually crowded with equipment and staff, e.g., nurses, doctors, etc., and the addition of operators to perform the ultrasound-guided procedure exacerbates the crowded condition.

Generally, it is not possible for the ultrasound operator to work alone and eliminate the need for three hands when using a conventional ultrasound system. For instance, setting the display device on the bed or patient is not a good solution, since this can cause strain to the operator's neck when looking back and forth from the procedure site (e.g., the needle insertion point) and the display device/ultrasound machine. Moreover, the operator may need to put the interventional instrument (e.g., needle) down to make adjustments on the display device (such as gain or depth), which can contaminate the interventional instrument. Furthermore, touching the display device/ultrasound machine can introduce further contamination. When ultrasound is not used, or poorly used, for vascular access, patients often suffer multiple needle insertions, further increasing the risk of infection.

Consequently, conventional ultrasound systems may not be well suited to ultrasound-assisted procedures. Moreover, use of conventional ultrasound systems for ultrasound-assisted procedures can result in a crowded and dangerous environment and introduce safety concerns for the patient. Hence, the patient may not receive the best care possible.

SUMMARY

A wearable ultrasound device and method for using the same are disclosed. In some embodiments, the wearable ultrasound device includes an ultrasound transducer configured to transmit ultrasound signals and receive reflected ultrasound based on the ultrasound signals and a fastener configured to secure the wearable ultrasound device proximate to a procedure site. The wearable ultrasound device can also include a processor configured to generate, based on the reflected ultrasound, patient data and a display device implemented to display a visual representation of the patient data.

In some other embodiments, an operator-worn ultrasound device includes an ultrasound transducer configured to transmit ultrasound signals at a patient anatomy and receive reflected ultrasound from the patient anatomy and a fastener configured to secure the operator-worn ultrasound device to an operator of the operator-worn ultrasound device while permitting the operator to, with one hand, grip a patient and operate the ultrasound transducer. The operator-worn ultrasound device can also include a processor configured to generate, based on the reflected ultrasound, a visual representation that describes the patient anatomy.

In some other embodiments, a patient-worn ultrasound device includes an ultrasound transducer configured to transmit ultrasound signals at a patient anatomy and receive reflected ultrasound from the patient anatomy and a fastener configured to secure the patient-worn ultrasound device to a patient while permitting the patient to operate the ultrasound transducer with one hand and adjust a display device with the other hand. The patient-worn ultrasound device can also include a processor configured to generate, based on the reflected ultrasound, a visual representation that describes the patient anatomy.

Other systems, machines and methods for a wearable ultrasound device are also described.

BRIEF DESCRIPTION OF THE DRAWINGS

The appended drawings illustrate examples and are, therefore, exemplary embodiments and not considered to be limiting in scope.

FIG. 8 illustrates other examples of a wearable ultrasound device displaying visual representations for another procedure.

FIG. 11 illustrates a data flow diagram of a method performed by an operator-worn ultrasound device.

FIG. 12 illustrates a data flow diagram of a method performed by a patient-worn ultrasound device.

DETAILED DESCRIPTION

Figure 1:
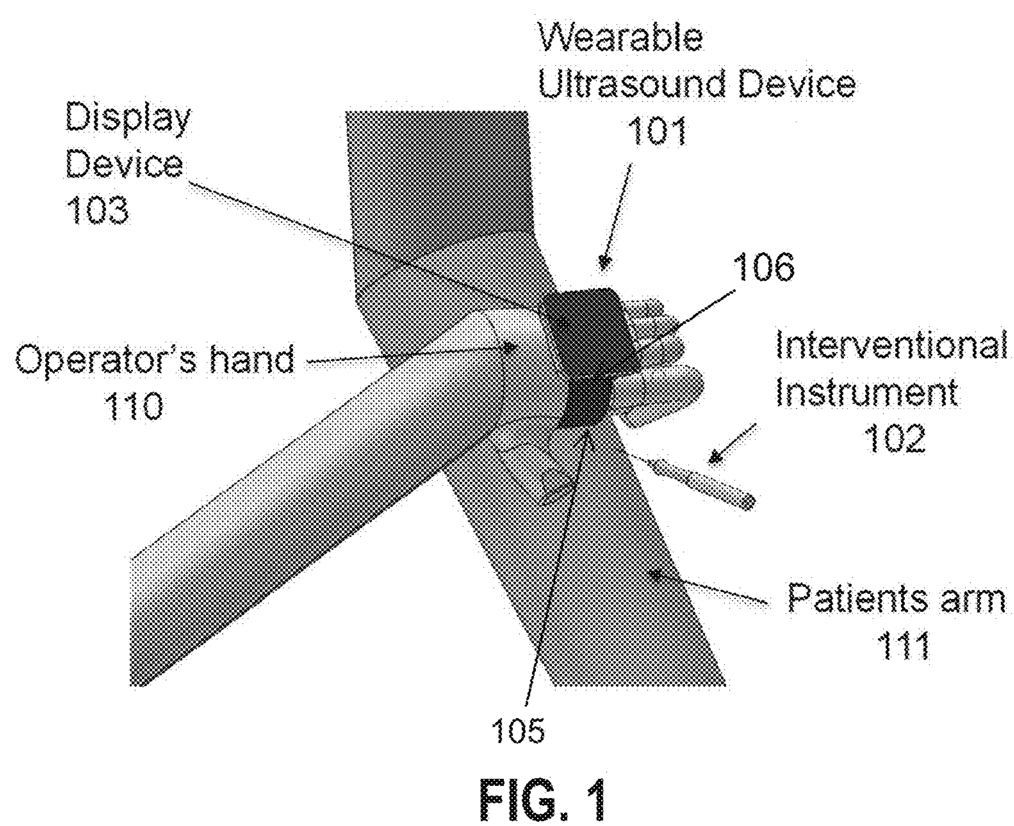
FIG. 1 illustrates an operator wearing a wearable ultrasound device in accordance with some embodiments.

In the following description, numerous details are set forth to provide a more thorough explanation of the embodiments described herein. It will be apparent, however, to one skilled in the art, that the embodiments may be practiced without these specific details. In other instances, well-known structures and devices are shown in block diagram form, rather than in detail, in order to avoid obscuring the techniques disclosed herein.

Systems, devices, and techniques are disclosed herein that include wearable ultrasound devices that can free-up an operator's hand compared to conventional ultrasound systems. In one embodiment, an operator (e.g., clinician or sonographer) wears an ultrasound device on one hand that is also used to hold the patient's arm. In another embodiment, the patient wears the ultrasound device, e.g., on their arm, proximate to the procedure site, such as a needle insertion point. As used herein, the term "operator" refers to a nurse, doctor, clinician, sonographer and the like, and does not include the patient. These devices can overcome the limitations of conventional ultrasound systems that are not well suited to ultrasound-assisted procedures.

The ultrasound systems disclosed herein include wearable ultrasound devices and can be used to assist various types of procedures, including vascular access, insertion of an interventional instrument (e.g., a needle, catheter, etc.), intravenous line (IV) placement, physical therapy, assessment of an injury and its healing, medication ingestion and activation, ascertaining vital statistics (e.g., blood pressure, temperature, pulse rate, pulse oxygenation levels, etc.), such as, for example, described below in more detail. In some embodiments, the ultrasound systems disclosed herein can be used in a pre-scan imaging stage prior to performing a procedure. In some embodiments, the ultrasound systems disclosed herein can be used during the procedure. In some examples, the ultrasound systems can be used by an operator who may not be a trained sonographer, such as, for example, a nurse. In some examples, the ultrasound systems can be used by a patient for whom the procedure is performed.

Operator Worn and Patient Worn Ultrasound Devices

The ultrasound systems disclosed herein include wearable ultrasound devices that can take any suitable form factor. In some embodiments, the wearable ultrasound device includes a band that can be placed over a person's body part, such as over an arm, leg, head, neck, torso, etc. In some other embodiments, the wearable ultrasound device includes a vest that can be placed over (or around) a person's torso. In yet some embodiments, the wearable ultrasound device includes a helmet, cap, and/or hat that can be worn on a person's head. In In still other embodiments, the wearable ultrasound device includes a patch that can be placed on any suitable body part, such as over a person's stomach to assist in determining if medications have been ingested (described below in more detail).

In some embodiments, the wearable ultrasound device is worn by an operator of the ultrasound system. Additionally or alternatively, the wearable ultrasound device can be worn by a patient. For example, FIG. 1 illustrates an example in which the wearable ultrasound device is worn by an operator of the ultrasound system. As mentioned above, as used herein, the term "operator" refers to a nurse, doctor, clinician, sonographer, and the like, and excludes the patient for whom the ultrasound procedure is performed. Referring to FIG. 1, the operator wears an ultrasound device 101 on their hand 110, and the ultrasound device 101 includes one or more transducer arrays configured to transmit ultrasound into, and receive reflected ultrasound from, the patient's arm 111. For instance, a transducer array (not shown) can be located on the bottom 105 of the band of the wearable ultrasound device 101, making contact with the patient's arm 111. In some embodiments, flexible bands couple the transducer array to the upper portion of the wearable ultrasound device 101 that is on top of the operator's hand 110. The wearable ultrasound device 101 can include a display device 103 that can display any suitable data, such as an ultrasound image, guidance on how to move the interventional instrument, an indication of an insertion point for the interventional instrument 102, an indication that the instrument 102 and wearable ultrasound device 101 are properly positioned for the procedure (e.g., a "proceed with the procedure" icon), patient data (e.g., biometric data other than ultrasound data), etc. As shown in FIG. 1, a display device 103 is on a top 106 of the band.

By placing the wearable ultrasound device 101 on the operator's hand 110, the operator's hand 110 not only holds the wearable ultrasound device 101, but can also be used to stabilize the patient's arm 111 and reduce the degrees of freedom for stabilizing the wearable ultrasound device 101. In this manner, the wearable ultrasound device 101 can be secured in place. This operation enhances the likelihood of a successful procedure and reduces the chance of needing to repeat the insertion of the interventional instrument 102. This extra stability from the operator's hand 110 is simply not possible with a conventional ultrasound system in which the operator's hand is needed at the ultrasound machine/display device that is not near the procedure site (e.g., a location on the patient's arm 111 including the insertion point for the interventional instrument 102). Hence, the ultrasound system with the wearable ultrasound device 101 provides significant advantages compared to conventional ultrasound systems. Moreover, the operator does not need to turn their head from the procedure site to view the wearable ultrasound device 101 (as is generally required with conventional ultrasound systems). This advantage reduces operator fatigue.

Figure 2:
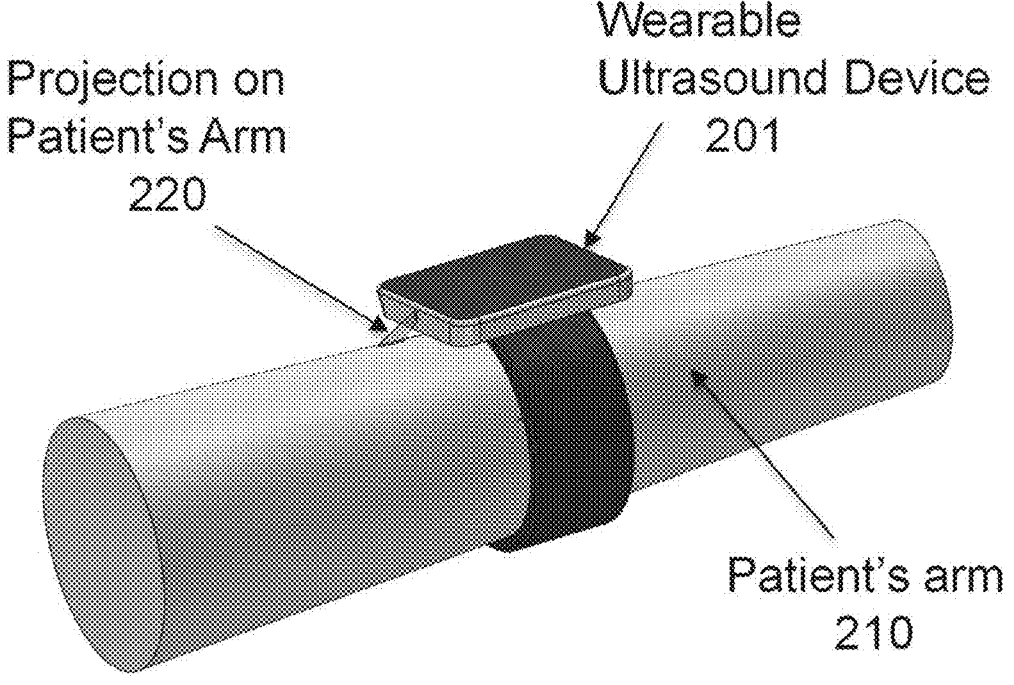
FIG. 2 illustrates a patient wearing a wearable ultrasound device in accordance with some embodiments.

In some embodiments, the patient can operate the wearable ultrasound device. Hence, the ultrasound system can be used for home care and/or remote/telemedicine. Although not illustrated in FIG. 1, the wearable ultrasound device 101 can include a projector (e.g., a MEMS device) that projects an image, shape, line, point, etc. on the patient's arm to further illustrate the patient's anatomy and/or insertion point for the interventional instrument. FIG. 2 illustrates some embodiments of a wearable ultrasound device with a projector. Referring to FIG. 2, wearable ultrasound device 201 is on a patient's arm 210 and includes a projector (e.g., a MEMS device) that makes a projection 220 on patient's arm 210. Projection 220 can be an image, shape, line, point, etc. as described above.

Figure 3:
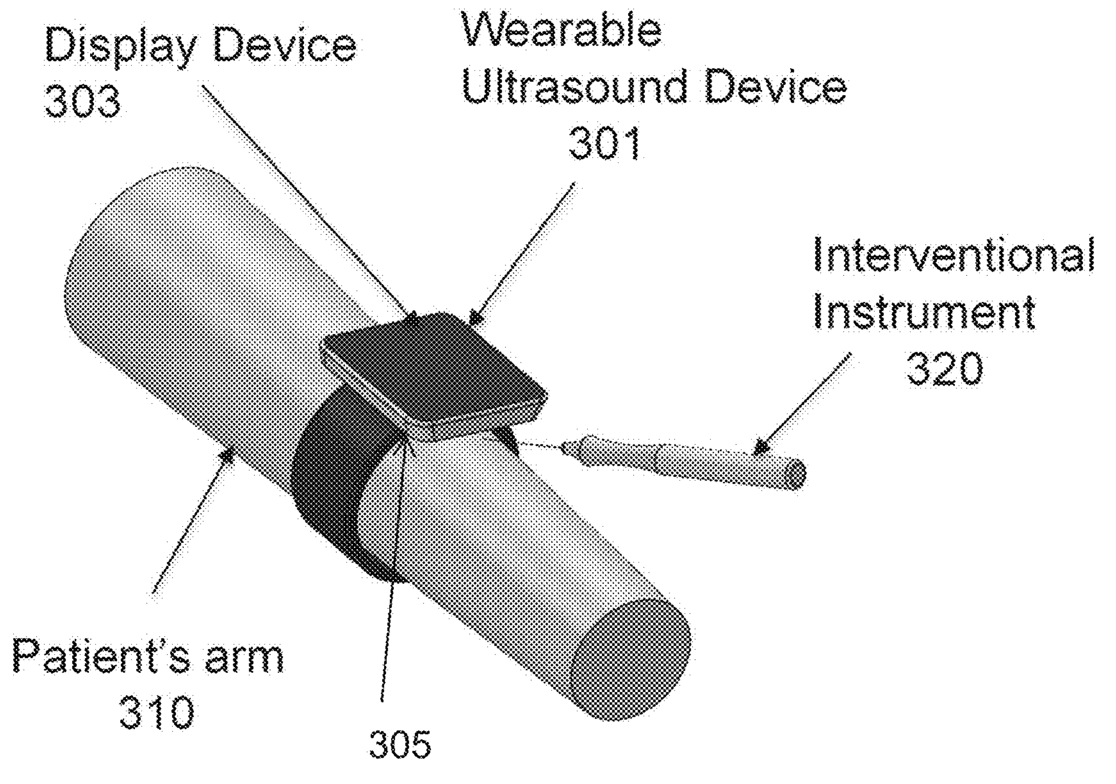
FIG. 3 illustrates some embodiments in which the wearable ultrasound device is worn by a patient.

FIG. 3 illustrates some embodiments in which the wearable ultrasound device is worn by a patient. In FIG. 3, the patient wears a wearable ultrasound device 301 on their arm 310, proximate to the procedure site (e.g., insertion site of an interventional instrument 320). In some embodiments, the wearable ultrasound device 301 includes an array of transducers on any suitable portion of the wearable ultrasound device 301. In some embodiments, the wearable ultrasound device 301 includes transducers 305 that are near or in contact with the skin of the patient's arm 310, such as around 360 degrees of the inside of the band of the wearable ultrasound device 301 and/or at the bottom of the wearable ultrasound device 301 (e.g., underneath the display device 303 and facing the patient). By combining ultrasound data from multiple transducers, the wearable ultrasound device 301 can generate a three-dimensional (3D) ultrasound image. In some embodiments, the wearable ultrasound device 301 includes a display device 303 to display the ultrasound image, including the 3D ultrasound image. Additionally or alternatively, the display device 303 can display patient data (e.g., biometric data, such as ECG data, pulse data, an oxygenation level, etc.). In an example, the display device 303 is above all or a portion of the transducer array 305.

Figure 4:
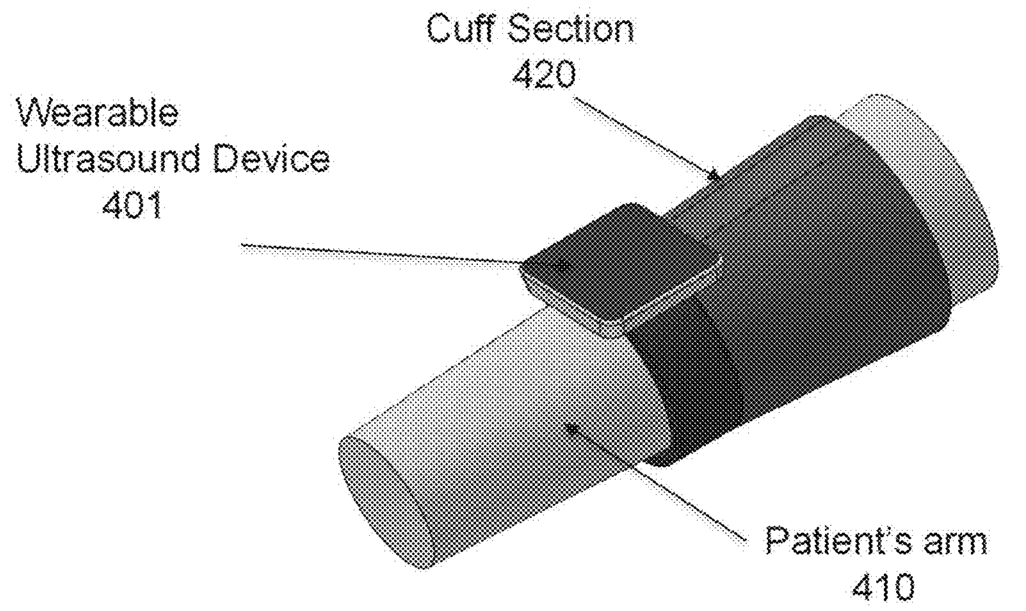
FIG. 4 illustrates some embodiments of a wearable ultrasound device with a strap, or cuff.

The wearable ultrasound device 301 can include a strap (or cuff) having sufficient width to include multiple sections. FIG. 4 illustrates some embodiments of a wearable ultrasound device with a strap, or cuff. Referring to FIG. 4, wearable ultrasound device 401 is on a patient's arm 410 and includes a first section that is a cuff section 420. A first section of the strap can apply pressure to the patient and be located above (with respect to the direction of blood flow) a procedure site (e.g., an insertion point for an interventional instrument, peripheral intravenous insertion site, etc.). The pressure can be applied to a blood vessel for cannulation of the blood vessel at the procedure site. In some embodiments, the strap is inflatable and uses sensors like a blood pressure cuff to expand and apply an amount of pressure to a portion of the patient to produce the intended result to help with the procedure being performed. In some embodiments, the ultrasound device provides feedback indicative of an amount of pressure applied and/or blood vessel compression. Hence, the ultrasound device can help apply pressure to a blood vessel so that the insertion point for an interventional instrument is easily detectable (by the operator and/or automatically by the ultrasound device). A second section of the strap/cuff can include a display device and be located proximate to the procedure site.

Pre-Scan and Concurrent-Scan Modes

Figure 5:
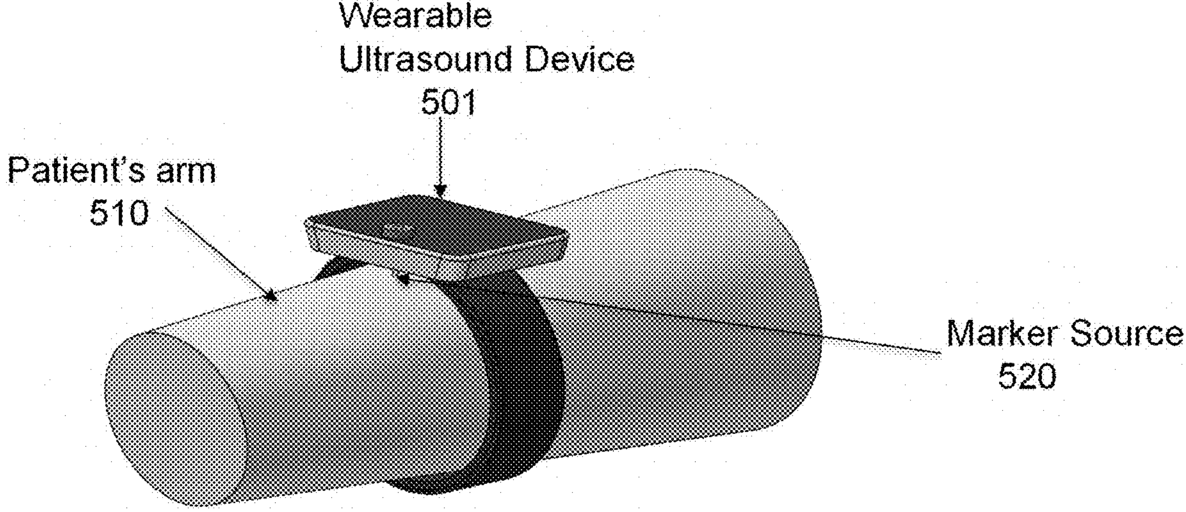
FIG. 5 illustrates some embodiments of a wearable ultrasound device with a marker source.

In some embodiments, the wearable ultrasound device can be used in a pre-scan mode to generate ultrasound data (e.g., image data) prior to the actual procedure, and be removed for the procedure. For example, the ultrasound device can be set at an initial position on a patient, such as on the patient's arm. In some embodiments, the ultrasound system can include a registration system that locates the ultrasound device with respect to the patient. For instance, the registration system can place one or more fiducial markers (such as three fiducial markers) on a patient, and the location of the ultrasound device on the patient can be determined from the distances and orientation of the ultrasound device to the fiducial markers. The ultrasound system can automatically move, or the operator or patient can manually move, the ultrasound device from the initial position across the patient, such as down the patient's arm. While the ultrasound device is being moved, the ultrasound device can generate image data of the patient's anatomy, such as to identify a blood vessel for needle insertion. In some embodiments, the ultrasound device generates image data (e.g., consecutive frames of ultrasound image data, etc.) and makes a determination based on the image data on whether to reposition the ultrasound device to another location on the patient (e.g., patient's arm, etc.) for a procedure. In some embodiments, the ultrasound device marks the patient based on the image data regarding the anatomy as it is moved. For instance, the ultrasound device can draw on the patient with ink the patient anatomy, including blood vessels. FIG. 5 illustrates some embodiments of a wearable ultrasound device with a marker source. Referring to FIG. 5, wearable ultrasound device 501 is on a patient's arm 510 and includes marker source 520 (e.g., ink source, etc.).

In some embodiments, the wearable ultrasound device determines a region to mark a patient. For instance, suppose a lesion (e.g., mole, skin cancer, cyst, etc.) is to be removed as part of the procedure. In some embodiments, the wearable ultrasound device can image the patient in the area of the lesion, and process the images with a neural network implemented to generate a region about the lesion, such as, for example, a circle of a certain radius selected so that if skin within the circle is removed, an acceptable surgical margin is obtained. The wearable ultrasound device can then mark the patient with the circle, e.g., with ink.

After the pre-scan stage is completed, the ultrasound device can be removed (e.g., removed from the patient) and the procedure can be commenced. In some embodiments, the ultrasound system can determine the position of the interventional instrument relative to the patient using the registration system. Using data generated during the pre-can stage, such as a desired insertion point for an interventional instrument, and/or the registration system, the operator can position the interventional instrument at the desired point and perform the procedure. In some embodiments, the registration system can be used in combination with image data placed (e.g., painted, such as with ink) on the patient. For example, the operator can guide the interventional instrument to the insertion point indicated with the registration system, and visually inspect the image data placed on the patient to make sure the insertion point indicated by the registration system matches the insertion point indicated by the image data.

Figure 6:
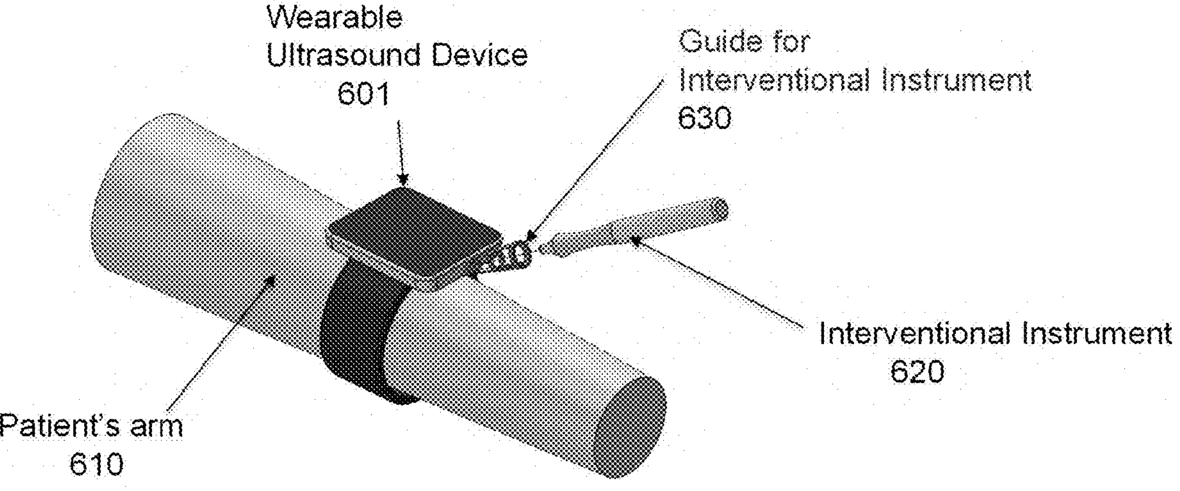
FIG. 6 illustrates some embodiments of a wearable ultrasound device with a guide for an interventional instrument.

In some embodiments, the wearable ultrasound device is used concurrently when the procedure is performed. For example, the ultrasound device can include one or more guides through which an interventional instrument can be inserted into a patient. For instance, the guides can include through-holes of various diameters corresponding to different needle gauges, and the through-holes can be placed at various angles (relative to the patient). As an example, the through-holes can be placed perpendicular to the patient (i.e., at 90 degrees), at 30 degrees, 60 degrees, 15 degrees, etc. In some embodiments, the guides can be removably attached to the ultrasound device for modularity, to accommodate various size through-holes for different gauge needles or interventional instruments, and at various angles (both with respect to the patient and rotationally, e.g., in azimuth and elevation). In some embodiments, the wearable ultrasound device provides real-time feedback to the user by using the guide to indicate which angle to use or whether the angle that is to be used is the proper angle for the needle or instrument. FIG. 6 illustrates some embodiments of a wearable ultrasound device with a guide for an interventional instrument. Referring to FIG. 6, wearable ultrasound device 601 is on a patient's arm 610 and includes guide 630 for an interventional instrument, such as interventional instrument 620.

In some embodiments, a user (e.g., ultrasound operator or the patient) can move the wearable ultrasound device and the ultrasound device can generate image data as it is moved. Based on the image data (e.g., blood vessel size, depth, etc.) and the interventional instrument (e.g., gauge and length), the ultrasound device can guide the user to place the ultrasound device at a location on the patient so that the guide (e.g., one of the though-holes) is positioned so that an interventional instrument when placed through the guide will be inserted at the desired position on the patient. In some embodiments, the ultrasound device indicates when the ultrasound device is properly positioned by illuminating lights around or near one of the through-holes (guides). In some embodiments, the ultrasound device includes one or more neural networks to process the image data and determine the proper positioning of the ultrasound device. In some embodiments, the ultrasound device includes a display device (e.g., the display device 303) that displays an ultrasound image that simultaneously depicts the patient's anatomy and the interventional instrument during insertion.

In some embodiments, the wearable ultrasound device includes a robotic component, such as, for example, an automatic needle insertion device. For instance, the wearable ultrasound device can include a tube through which a patient can insert an appendage, such as an arm. As described above, in some embodiments, the wearable ultrasound device automatically determines a desired insertion point for the needle, based on ultrasound images and processing of the ultrasound images with a neural network, and then the wearable ultrasound device can move the robotically controlled needle to the insertion point automatically, (e.g., via mechanical movement mechanisms, such as rails, levers, cables, grooves, etc.) and perform the injection automatically.

A Display Device

In some embodiments, the ultrasound system includes any suitable display device. As previously mentioned, the wearable ultrasound device can include a display device, such as the display device 103 in FIG. 1 and the display device 303 in FIG. 3. In some embodiments, the display device includes a hologram projector that projects a hologram of the ultrasound image (e.g., a 3D representation of the patient's anatomy simultaneously with the interventional instrument in hologram form), viewable to the operator of the ultrasound device so that the operator can simultaneously see the hologram, the interventional instrument, and the procedure site.

Additionally or alternatively, the display device can include a display screen (e.g., an LCD screen, a touchscreen, etc.). In some embodiments, the display screen is implemented to display an ultrasound image, such as a B-mode image, a C-mode image, an M-mode image, and/or a 3D image. Additionally or alternatively, in some embodiments, the display screen can be implemented to display data other than an ultrasound image. For example, the display screen can display patient biometric data from one or more biometric sensors that are separate from, and/or integrated with, the wearable ultrasound device. For instance, the ultrasound device can include a blood pressure cuff, and the display screen can display a patient's blood pressure. Other examples of biometric data that can be displayed by the wearable ultrasound device include heart/pulse rate, blood oxygenation levels, an amount of blood vessel compression/constriction, blood flow rate, temperature, respiration, spectral data (e.g., indicating blood content and/or chemical elements), etc.

In some embodiments, the display device of the wearable ultrasound device is implemented to display data other than patient biometric data. For instance, the ultrasound device can include one or more neural networks configured to process one or more ultrasound images and generate an inference based on the images. The inference can include a probability, such as a probability that the images indicate a trauma, injury, lesion, cancer, and the like. In one example, the ultrasound images can be acquired over a time period, such as multiple days or weeks, and the inference can include an expected date at which the injury is expected to be sufficiently healed. For instance, the patient may be a professional athlete who wears the ultrasound device to generate images of a pulled muscle. Such images can be reviewed by a physician or with an automated system (e.g., neural network, machine learning, artificial intelligence) to enable a determination of an expected date at which the injury is expected to be sufficiently healed. In some embodiments, the neural network process the images and generate an expected amount of time (in days or a calendar date) until the muscle is healed and the athlete can return to competition, and the display device can display the amount of time to the athlete. In some embodiments, the neural network is part of the wearable ultrasound device. For example, the neural network can be implemented with an application-specific integrated circuit (ASIC) that is included in the wearable ultrasound device.

In some embodiments, the wearable ultrasound device can display a performance-measurement data indicator. Suppose a patient wants to know if they are correctly exercising/working out, such as a baseball player who exercises their arm. In some embodiments, the wearable ultrasound device can be implemented to image a muscle, determine a size of the muscle, and display an indication of the muscle size. Hence, the patient can be confident that they are properly exercising the muscle. In an example, suppose the patient has recently undergone a surgery, such as Tommy John surgery to repair a torn ulnar collateral ligament inside the elbow. The patient wants to make sure during physical therapy that they are doing the proper movement. In some embodiments, the wearable ultrasound device provides ultrasound-based feedback, such as image data or parameters of the repaired ligament, to guide the patient to perform the proper physical therapy for proper healing of the ligament. Additionally or alternatively, the display device can display an indication that exercises are correctly or incorrectly performed by the patient, guidance on how to change/improve an exercise, etc.

In some embodiments, the display device displays an indication of medication in a patient's blood stream, such as an amount of the medication, a binary indication that the medication is present in the blood stream, or an indication that the medication is activated (e.g., from ultrasound or heat applied by the wearable ultrasound device, as described below in more detail). In some embodiments, the ultrasound device determines the medication is in a particular location by identifying markers (e.g., via ultrasound images, via sensor data from one or more other sensors on the ultrasound device, etc.). Example markers are described below in more detail. In some embodiments, the ultrasound device can be used to trigger a heat-activated medication. The heat-activated medication can be activated by the ultrasound device using heat provided by a heat source of the ultrasound device or via radio-frequency (RF) energy transmitted by the ultrasound device when the medication is in particular region of interest as indicated by the ultrasound device (e.g., via ultrasound images, via sensor data from one or more other sensors on the ultrasound device, etc.).

Figure 7:
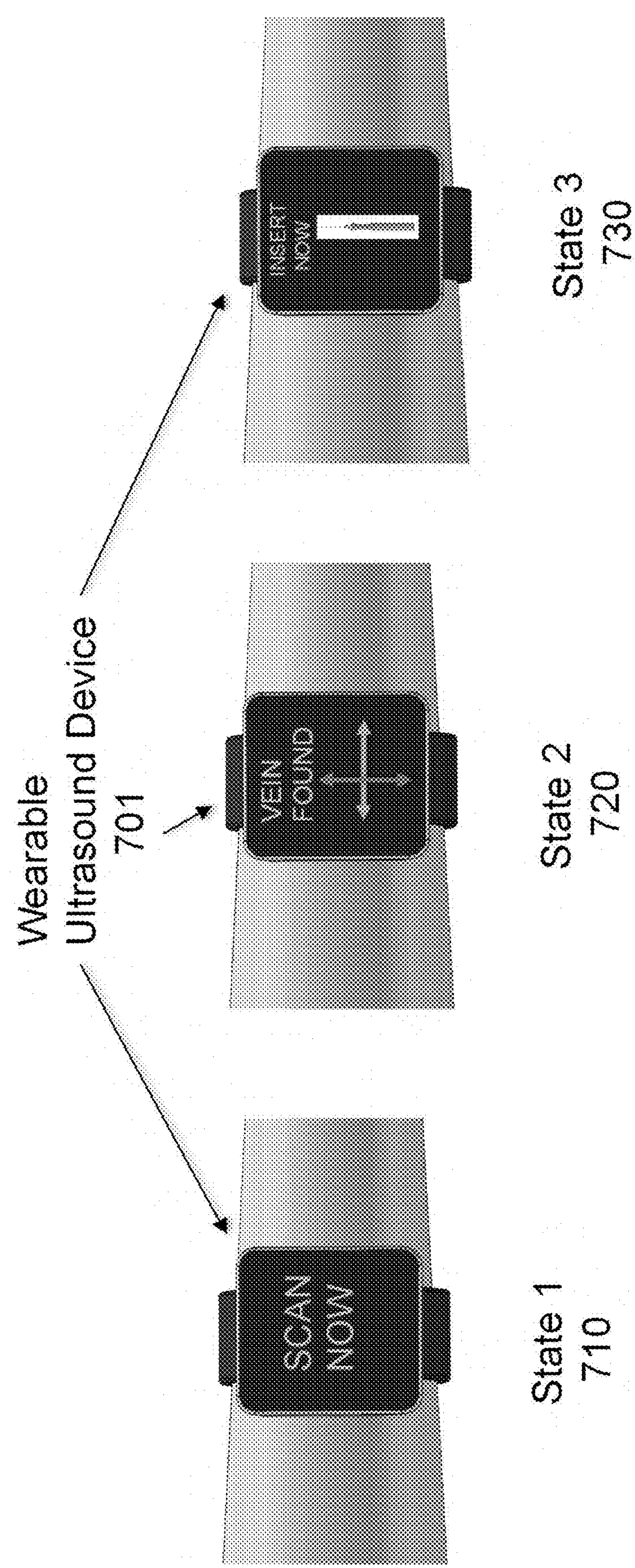
FIG. 7 illustrates some embodiments of a wearable ultrasound device displaying visual representations for a procedure.
Figure 8:
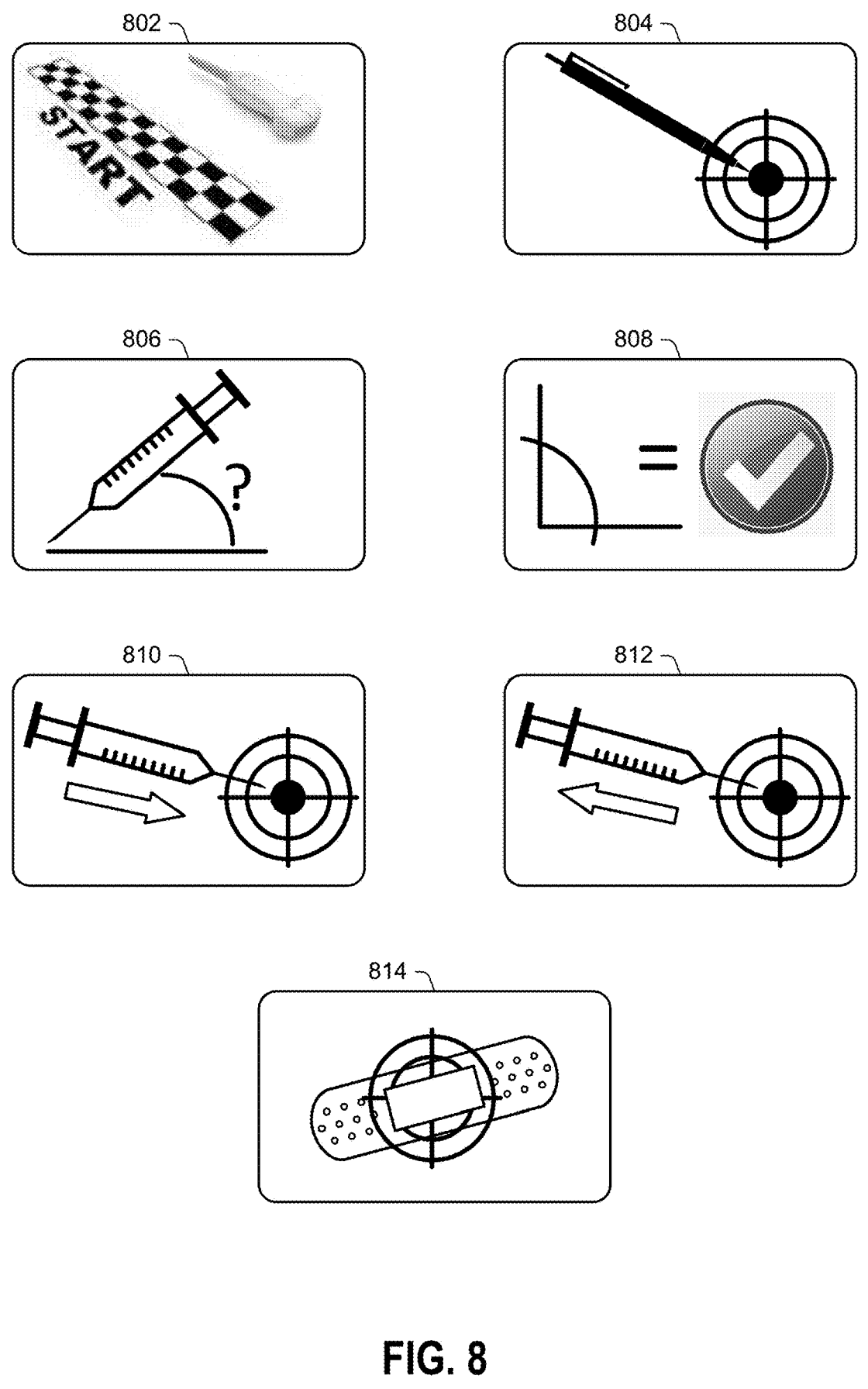

In some embodiments, the display device of the ultrasound system, such as a display device of the wearable ultrasound device, can display a series of visual representations, such as icons, cartoons, animations, images, and the like, to instruct the user how to proceed. Hence, the wearable ultrasound device can display steps (e.g., steps of a flow diagram) for a given procedure or ultrasound protocol. FIG. 7 illustrates some embodiments of a wearable ultrasound device displaying visual representations for a procedure. Referring to FIG. 7, wearable ultrasound device 701 displays visual representations of states 1-3 for a procedure on its display, including a scan now state 710, a vein found state 720, and an insert now state 730 (for inserting, for example, an interventional instrument). FIG. 8 illustrates other examples including, for a procedure of a needle insertion, in some embodiments, the wearable ultrasound device can display a first visual representation (802) indicating to scan the patient's arm. When completed, the ultrasound device can display a second visual representation (804) indicating to initiate a process to mark an injection point. When completed, the ultrasound device can display a third visual representation (806) indicating to set an angle of the needle. When completed, the ultrasound device can display a fourth visual representation (808) (e.g., a green light) indicating the angle is correct. When completed, the ultrasound device can display a fifth visual representation (810) to insert the needle. When completed, the ultrasound device can display a sixth visual representation (812) to remove the needle. When completed, the ultrasound device can display a seventh visual representation (814) to place a bandage over the insertion point, and the like.

As described above, the wearable ultrasound device can include a display device. Additionally or alternatively, the ultrasound system can include a display device that is separate from the wearable ultrasound device and that is implemented to display information based on data obtained from the wearable ultrasound device. Hence, the wearable ultrasound device can be in communication with the display device, such as via a wired, wireless, or combination thereof communication link. The display device can include a smart phone, tablet, ultrasound machine, glasses, monocle, heads-up display, contact lenses, and the like. In an example, the display device, such as a pair of smart-glasses, displays an AR/VR environment that includes at least one virtual marking (such as an insertion point for an interventional instrument) and an image of the patient. As the operator moves or repositions the glasses, the virtual marking can remain at a fixed position on the patient, similar to a red dot sight. The location of the virtual marking can be determined by the ultrasound system, as previously described with respect to a needle insertion point.

Capabilities of the Wearable Ultrasound Device

Figure 9:
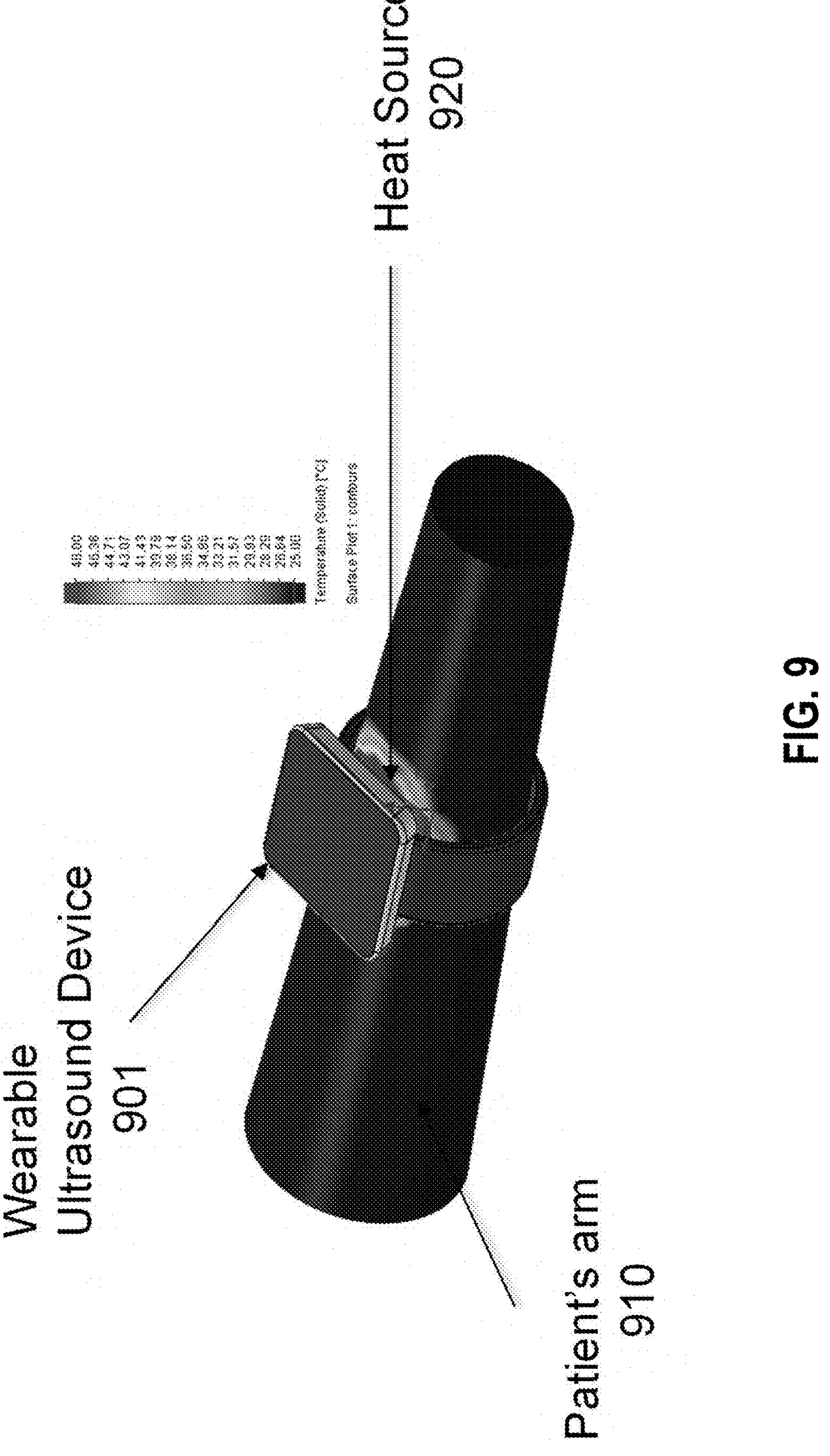
FIG. 9 illustrates some embodiments of a wearable ultrasound device with a heat source.

As described above, in some embodiments, the wearable ultrasound device includes any number and type of transducer arrays, configured in any physical layout on or in the wearable ultrasound device. Additionally, in some embodiments, the wearable ultrasound device includes one or more sensors/and or one or more sources to implement any suitable function. In one example, the wearable ultrasound device includes a heat source and a temperature sensor (e.g., thermometer). The heat source can be implemented to direct heat into a patient. In an example, the heat source includes a HIFU heat source. HIFU heat sources can generate significant amounts of heat quickly (e.g., 70 degrees C. in less than one second), causing biological tissues where the heat is focused to shrink and fuse together, stopping bleeding. FIG. 9 illustrates some embodiments of a wearable ultrasound device with a heat source. Referring to FIG. 9, wearable ultrasound device 901 is on a patient's arm 910 and includes heat source 920.

The heat source can also be used to enhance healing of an injury. For instance, a physical therapist usually administers heat in a broad area, with no data indicating that the heat is reaching the trauma. By combining the use of the heat source with ultrasound images captured by the wearable ultrasound device, the therapist can focus the heat at the trauma and see in real time the effects of the heat. In some embodiments, the display device displays guidance to the therapist to direct the heat in a certain direction so that it is focused at the trauma. In some embodiments, the display device also displays a temperature read by the thermometer integrated with the wearable ultrasound device.

In some embodiments, the wearable ultrasound device includes a cold source implemented to generate cold temperatures. Hence, the cold temperatures can be directed, e.g., by a physical therapist or the patient, at an injury, allowing the user to switch between applying hot with the heat source and cold with the cold source directed at the injury, and thereby improving the healing process. In an example, the cold generated by the cold source is applied during the administration of chemotherapy. By directing cold at tissue, e.g., nerve endings, neuropathy caused by chemotherapy can be reduced or eliminated. By monitoring the tissue via images generated by ultrasound simultaneously with the application of cold, the cold can be directed at affected tissue before the onset of neuropathy at the tissue.

In some embodiments, the wearable ultrasound device includes a blood pressure device, such as a blood pressure cuff, configured to measure a patient's blood pressure. Usually, blood pressure devices inflate a bladder to a predetermined pressure to initiate the measurements. However, for some patients, such as elderly patients with sensitive blood vessels, the initial pressure can be high enough to cause discomfort or damage to the blood vessels. Hence, the wearable ultrasound device can control the pressure of the blood pressure device based on ultrasound data. For instance, in some embodiments, the wearable ultrasound device directs ultrasound at the blood vessels and based on the reflections, determines an amount of compression of the blood vessels caused by the blood pressure device. As an example, in some embodiments, the wearable ultrasound device includes one or more neural networks configured to process one or more ultrasound images of blood vessels and generate an amount of blood vessel compression. If the compression reaches a threshold amount of compression, (e.g., as a percentage of an initial diameter, or an absolute diameter size), the wearable ultrasound device can stop the blood pressure device from inflating, and thus reduce or even prevent damage to the patient's blood vessels.

In some embodiments, the wearable ultrasound device includes sensors for determining a patient's vital signals, including blood pressure, heart rate, temperature, respiratory rate, and blood oxygenation. The sensor data can be displayed in any suitable format on a display device of the ultrasound system, such as on a display device included in or on the wearable ultrasound device.

In some embodiments, the wearable ultrasound device includes an inertial measurement unit (IMIU) that can communicate with the above-referenced registration system so that the location and orientation of the wearable ultrasound device can be determined in a coordinate system. An IMU can include a combination of accelerometers, gyroscopes, and magnetometers, and generate location and/or orientation data including data representing six degrees of freedom (6DOF), such as yaw, pitch, and roll angles in a coordinate system. Typically, 6DOF refers to the freedom of movement of a body in three-dimensional space. For example, the body is free to change position as forward/backward (surge), up/down (heave), left/right (sway) translation in three perpendicular axes, combined with changes in orientation through rotation about three perpendicular axes, often termed yaw (normal axis), pitch (transverse axis), and roll (longitudinal axis). Additionally or alternatively, the ultrasound system can include a camera to determine location and/or orientation data for the wearable ultrasound device.

In addition to the procedures aforementioned, such as vascular access, intervention instrument insertion, directed heat and cold, etc., the wearable ultrasound device facilitates numerous other medical procedures.

Medication Administration and Monitoring

In some embodiments, the wearable ultrasound device supports the administration of medication to a patient, and the monitoring of medication ingested by a patient. In an example, a medication can be activated by ultrasound and/or directed heat from the wearable ultrasound device. For instance, the medication can be administered via injection and/or orally. The medication can remain inert (inactive) until it is activated, such as by directing ultrasound and/or heat at blood vessels in the area of an injury. The activation can result from directed ultrasound, which unlocks an element or compound of the medication to make it active. In this way, the medication can be targeted to a specific area of the body.

In an example, a medication can include a marker that can be detectable by ultrasound. An example of a marker includes an ultrasound oscillator that generates ultrasound upon ingestion, a material that decays over time but is detectable before decay, or a material that results in different contrasts or colors in an ultrasound image. As the medication is ingested, such as via injection into the blood stream, the wearable ultrasound device can read the marker and determine an amount of the medication in the patient's blood stream. The amount can be displayed on a display device of the ultrasound system, e.g., on the wearable ultrasound device, and an operator or patient can control the dosage of the medication based on the detected amount of the medication read from the ultrasound.

In some embodiments, the wearable ultrasound device includes a patch that can be placed over a patient's stomach. When the patient takes medication in pill form, upon ingestion, a micro ultrasound oscillator within the pill is activated by the digestion process. In some embodiments, the wearable ultrasound device detects the ultrasound emitted from the pill to ascertain that the medication has been taken by the patient and then keeps a record of medications taken by the patient together with timestamps of the detection. Hence, the ultrasound system with the wearable ultrasound device can determine an actual medication record for the patient, compared to a prescribed record that may not include whether the medication was actually taken. This example is particularly important for many patients, such as elderly or forgetful patients, who do not always remember to timely take their medications.

IV Placement and Delivery

In some embodiments, the wearable ultrasound device facilitates the placement of an IV and the delivery of fluid via the IV. For example, the wearable ultrasound device can generate a measure of the patient's vascular patency of a patient's blood vessel (the degree to which a blood vessel is not blocked or obstructed), such as based on, for example, ultrasound images and a neural network that processes the images to generate the measure of vascular patency. A user, such as an EMT or clinician, can determine a proper blood vessel to administer the IV based on the measure of vascular patency generated by the wearable ultrasound device. For instance, if the blood vessel is too obstructed, the user can use a different blood vessel for the IV.

In an example, the wearable ultrasound device can generate a measure of flow rate (fluid speed) within a blood vessel based on ultrasound. The operator can adjust the flow rate of the IV based on the fluid speed in the blood vessel determined from the ultrasound.

Complications During Surgery

In some embodiments, the wearable ultrasound device can identify complications that can occur during a surgery, such as when the patient has a panic attack, or an allergic reaction to a medication. For example, as discussed above, the wearable ultrasound device can determine patient data including biometric data. The wearable ultrasound device can include a processor to monitor the patient data and determine whether a complication occurs during surgery, e.g., a panic attack or allergic reaction, such as by comparing the patient data over time to a stored record of data indicative of various complications that can occur during surgery. By matching the patient data to the stored data (or matching statistics of the data sets), the ultrasound system can generate, such as with a neural network implemented by the processor, a probability the patient is having an allergic reaction, a probability the patient is having a panic attack, etc. If a generated probability is above a threshold probability (e.g., 75%), then the ultrasound system can display a warning.

In some embodiments, the wearable ultrasound device is IPX7 rated, to facilitate easy cleaning. For example, the ultrasound device can be manufactured using low temperature silicone overmolding techniques that do not harm the internal battery of the device.

Exemplary Flow Diagrams

Figure 10:
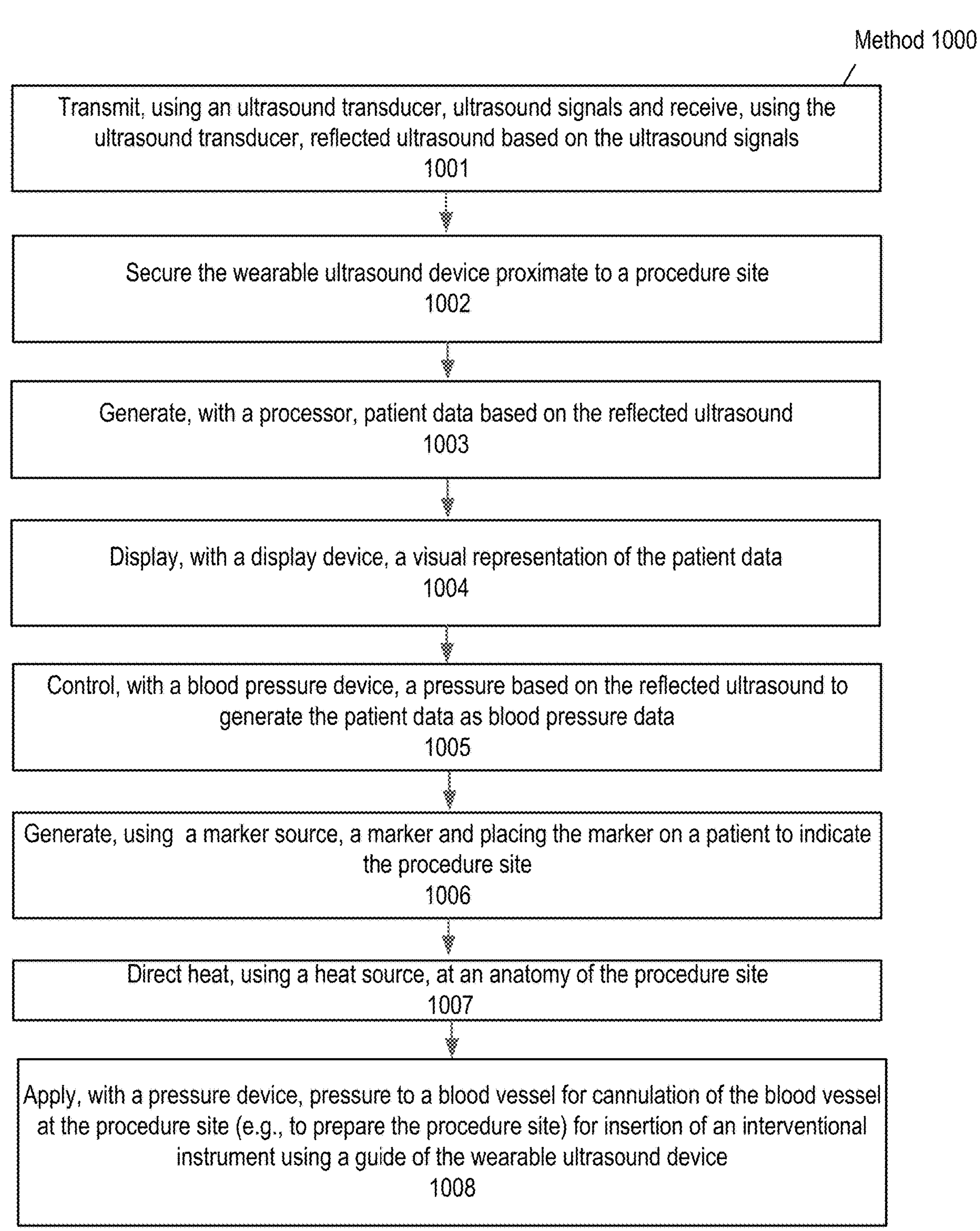
FIG. 10 illustrates a data flow diagram of a method performed by or in conjunction with a wearable ultrasound device.

FIG. 10 illustrates a data flow diagram of a method 1000 performed by or in conjunction with a wearable ultrasound device. Operations of the method are performed by processing logic that may comprise hardware (circuitry, dedicated logic, etc.), software (such as is run on a general-purpose computer system or a dedicated machine), firmware, or combinations thereof. In some embodiments, the wearable ultrasound device comprises one of the devices described above in conjunction with FIGS. 1-9.

Referring to FIG. 10, the method includes transmitting, with an ultrasound transducer, ultrasound signals and receive, with the ultrasound transducer, reflected ultrasound based on the ultrasound signals (block 1001). In some embodiments, the ultrasound transducer is implemented to transmit the ultrasound signals and receive the reflected ultrasound concurrently with a procedure performed at the procedure site.

The method also includes securing the wearable ultrasound device proximate to a procedure site (block 1002). In some embodiments, the wearable ultrasound device is secured proximate to a procedure site with a fastener. In some embodiments, the fastener is implemented to secure the wearable ultrasound device to an operator body part that is proximate to the procedure site of a patient body part. In some embodiments, the fastener is implemented to secure the wearable ultrasound device to a patient body part that is proximate to the procedure site. In some embodiments, the fastener is implemented to remove the wearable ultrasound device from proximity of the procedure site prior to a procedure being performed at the procedure site. In some embodiments, the procedure site corresponds to a peripheral intravenous insertion site, and the patient data includes a flow rate of fluid delivered by the peripheral intravenous insertion.

The method further includes, generating, with a processor, patient data based on the reflected ultrasound (block 1003). In some embodiments, the patient data indicates at least one of a medication ingestion and an activation of an ingested medication. In some embodiments, the patient data includes at least one of blood pressure data, a compression of a blood vessel, a blood vessel patency, a blood flow rate, and an indication of tissue repair.

The method also includes displaying, with a display device, a visual representation of the patient data (block 1004). In some embodiments, the display device is implemented to display guidance for a procedure at the procedure site. In some embodiments, the display device is implemented to display the visual representation without displaying an ultrasound image.

In some embodiments, the method includes controlling, with a blood pressure device, a pressure based on the reflected ultrasound to generate the patient data as blood pressure data (block 1005). In some embodiments, the pressure is the blood pressure of the patient associated with the patient data.

In some embodiments, the method includes, generating, using a marker source, a marker and placing the marker on a patient to indicate the procedure site (block 1006). In some embodiments, the marker source is implemented to generate the marker with at least one of ink and light. In some embodiments, the marker indicates an insertion point for an interventional instrument. In some embodiments, the processor is implemented to determine a surgical margin, and the marker indicates the surgical margin.

In some embodiments, the method also includes directing heat, using a heat source, at an anatomy of the procedure site (block 1007), applying, with a pressure device, pressure to a blood vessel for cannulation of the blood vessel at the procedure site (block 1008). In some embodiments, this is to prepare the procedure site for the insertion, using a guide, of an interventional instrument for insertion at the procedure site.

FIG. 11 illustrates a data flow diagram of a method 1100 performed by an operator-worn ultrasound device. Operations of the method are performed by processing logic that may comprise hardware (circuitry, dedicated logic, etc.), software (such as is run on a general-purpose computer system or a dedicated machine), firmware, or combinations thereof. In some embodiments, the wearable ultrasound device comprises one of the devices described above in conjunction with FIGS. 1-9.

Referring to FIG. 11, the method includes transmitting, with an ultrasound transducer, ultrasound signals at a patient anatomy and receiving, with the ultrasound transducer, reflected ultrasound from the patient anatomy (block 1101). The ultrasound transducer can be part of an operator-worn ultrasound device. The method also includes securing, with a fastener, the operator-worn ultrasound device to an operator of the operator-worn ultrasound device while permitting the operator to, with one hand, grip a patient and operate the ultrasound transducer (block 1102) and generating, with a processor, a visual representation that describes the patient anatomy based on the reflected ultrasound, a visual representation that describes the patient anatomy (block 1103).

FIG. 12 illustrates a data flow diagram of a method 1200 performed by a patient-worn ultrasound device. Operations of the method are performed by processing logic that may comprise hardware (circuitry, dedicated logic, etc.), software (such as is run on a general-purpose computer system or a dedicated machine), firmware, or combinations thereof. In some embodiments, the wearable ultrasound device comprises one of the devices described above in conjunction with FIGS. 1-9.

Referring to FIG. 12, the method includes transmitting, with an ultrasound transducer, ultrasound signals at a patient anatomy and receive, with the ultrasound transducer, reflected ultrasound from the patient anatomy (block 1201). The ultrasound transducer can be part of a patient-worn ultrasound device. The method also includes securing the patient-worn ultrasound device to a patient while permitting the patient to operate the ultrasound transducer with one hand and adjust a display device with the other hand (block 1202) and generating, with a processor, a visual representation that describes the patient anatomy based on the reflected ultrasound, a visual representation that describes the patient anatomy (block 1203).

Figure 13:
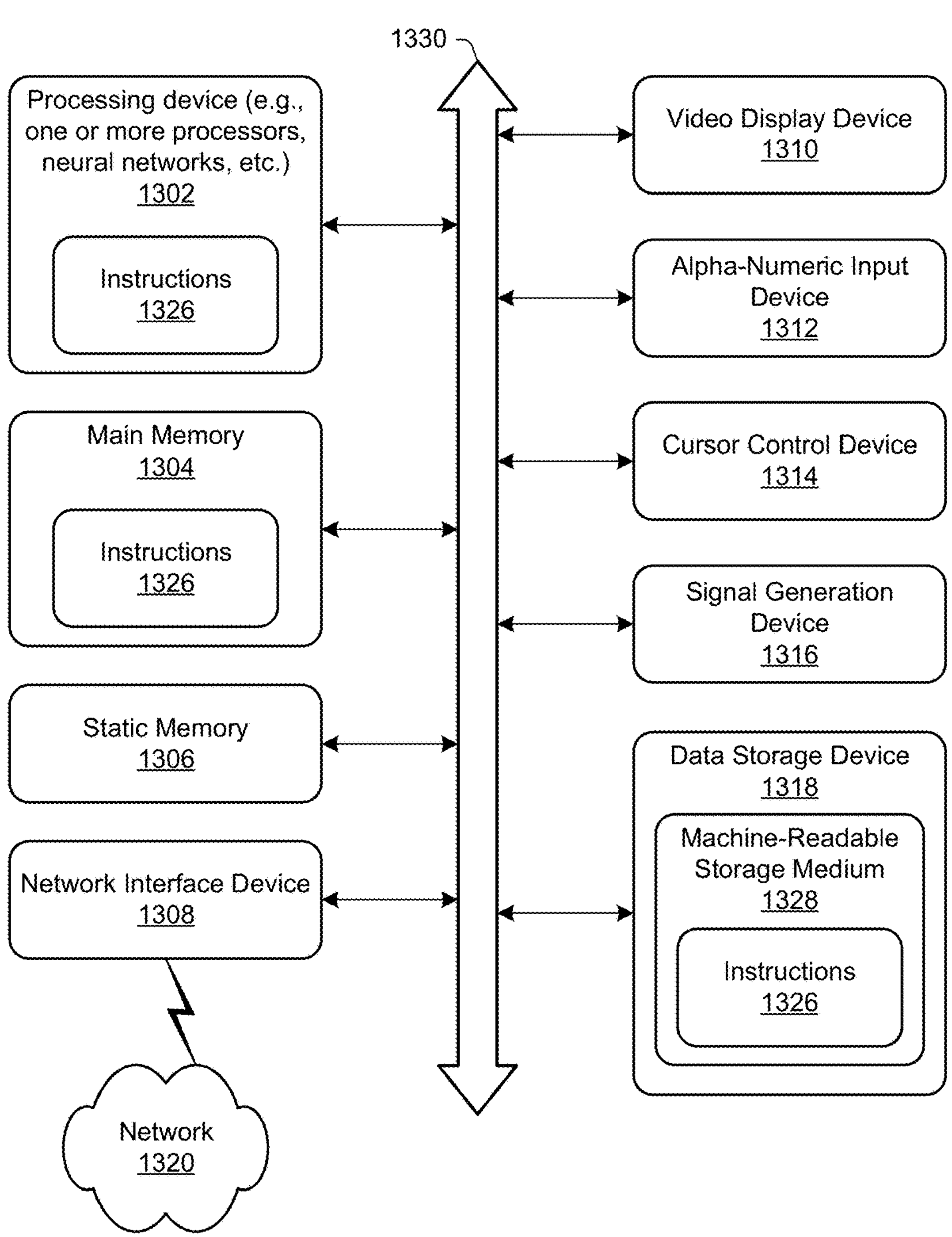
FIG. 13 illustrates a block diagram of an example computing device that can perform one or more of the operations described herein, in accordance with some embodiments.

FIG. 13 illustrates a block diagram of an example computing device 1300 that can perform one or more of the operations described herein, in accordance with some embodiments. Computing device 1300 can be connected to other computing devices in a LAN, an intranet, an extranet, and/or the Internet. The computing device can operate in the capacity of a server machine in client-server network environment or in the capacity of a client in a peer-to-peer network environment. The computing device can be provided by a personal computer (PC), a server computing, a desktop computer, a laptop computer, a tablet computer, a smartphone, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods and processes discussed herein. In some embodiments, the computing device 1300 can be one or more of an access point and a packet forwarding component.

The example computing device 1300 can include a processing device (e.g., a general-purpose processor, a PLD, etc.) 1302, a main memory 1304 (e.g., synchronous dynamic random-access memory (DRAM), read-only memory (ROM)), a static memory 1306 (e.g., flash memory and a data storage device 1318), which can communicate with each other via a bus 1330. Processing device 1302 can be provided by one or more general-purpose processing devices such as one or more microprocessors, central processing units, or the like. In an illustrative example, processing device 1302 can comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 1302 can also comprise one or more special-purpose processing devices such as an application specific integrated circuit (ASIC), a field programmable gate array (FPGA), a digital signal processor (DSP), network processor, or the like. In some embodiments, processing device 1302 includes one or more neural networks (e.g., machine learning neural networks, deep learning neural networks, etc.). The processing device 1302 can be configured to execute the operations described herein, in accordance with one or more aspects of the present disclosure, for performing the operations and steps discussed herein.

Computing device 1300 can further include a network interface device 1308 which may communicate with a network 1320. The computing device 1300 also can include a video display unit 1310 (e.g., a liquid crystal display (LCD) or a cathode ray tube (CRT)), an alphanumeric input device 1312 (e.g., a keyboard), a cursor control device 1314 (e.g., a mouse) and an acoustic signal generation device 1316 (e.g., a speaker, and/or a microphone). In an example, the alphanumeric input device 1312 includes a microphone to accept touchless input, e.g., spoken commands. In one embodiment, video display unit 1310, alphanumeric input device 1312, and cursor control device 1314 may be combined into a single component or device (e.g., an LCD touch screen).

Data storage device 1318 can include a computer-readable storage medium 1328 on which may be stored one or more sets of instructions 1326, e.g., instructions for carrying out the operations described herein, in accordance with one or more aspects of the present disclosure. For instance, the instructions 1326 can implement the operations described herein. Instructions 1326 can also reside, completely or at least partially, within main memory 1304 and/or within processing device 1302 during execution thereof by computing device 1300, main memory 1304 and processing device 1302 also constituting computer-readable media. The instructions can further be transmitted or received over a network 1320 via network interface device 1308.

While computer-readable storage medium 1328 is shown in an illustrative example to be a single medium, the term "computer-readable storage medium" should be taken to include a single medium or multiple media (e.g., a centralized or distributed database and/or associated caches and servers) that store the one or more sets of instructions. In some embodiments, the computer-readable storage medium 1328 implements the operations described above. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

There are a number of example embodiments described herein.

Example 1 is a wearable ultrasound device comprising: an ultrasound transducer configured to transmit ultrasound signals and receive reflected ultrasound based on the ultrasound signals; a fastener configured to secure the wearable ultrasound device proximate to a procedure site; a processor configured to generate, based on the reflected ultrasound, patient data; and a display device implemented to display a visual representation of the patient data.

Example 2 is the wearable ultrasound device of example 1 that may optionally include that the fastener is implemented to secure the wearable ultrasound device to an operator body part that is proximate to the procedure site of a patient body part.

Example 3 is the wearable ultrasound device of example 1 that may optionally include that the fastener is implemented to secure the wearable ultrasound device to a patient body part that is proximate to the procedure site.

Example 4 is the wearable ultrasound device of example 1 that may optionally include a blood pressure device, wherein the processor is implemented to control a pressure of the blood pressure device based on the reflected ultrasound to generate the patient data as blood pressure data.

Example 5 is the wearable ultrasound device of example 1 that may optionally include that the display device is implemented to display the visual representation without displaying an ultrasound image.

Example 6 is the wearable ultrasound device of example 1 that may optionally include a marker source implemented to generate a marker and place the marker on a patient to indicate the procedure site.

Example 7 is the wearable ultrasound device of example 6 that may optionally include that the marker source is implemented to generate the marker with at least one of ink and light.

Example 8 is the wearable ultrasound device of example 6 that may optionally include that the marker indicates an insertion point for an interventional instrument.

Example 9 is the wearable ultrasound device of example 6 that may optionally include that the processor is implemented to determine a surgical margin, and the marker indicates the surgical margin.

Example 10 is the wearable ultrasound device of example 1 that may optionally include that the procedure site corresponds to a peripheral intravenous insertion, and the patient data includes a flow rate of fluid delivered by the peripheral intravenous insertion.

Example 11 is the wearable ultrasound device of example 1 that may optionally include that the patient data indicates at least one of a medication ingestion and an activation of an ingested medication.

Example 12 is the wearable ultrasound device of example 1 that may optionally include a heat source implemented to direct heat at an anatomy of the procedure site.

Example 13 is the wearable ultrasound device of example 1 that may optionally include a pressure device implemented to apply pressure to a blood vessel for cannulation of the blood vessel at the procedure site.

Example 14 is the wearable ultrasound device of example 1 that may optionally include that the fastener is implemented to remove the wearable ultrasound device from proximity of the procedure site prior to a procedure being performed at the procedure site.

Example 15 is the wearable ultrasound device of example 1 that may optionally include that the ultrasound transducer is implemented to transmit the ultrasound signals and receive the reflected ultrasound concurrently with a procedure performed at the procedure site.

Example 16 is the wearable ultrasound device of example 1 that may optionally include that a guide for an interventional instrument for insertion at the procedure site.

Example 17 is the wearable ultrasound device of example 1 that may optionally include that the patient data includes at least one of blood pressure data, a compression of a blood vessel, a blood vessel patency, a blood flow rate, and an indication of tissue repair.

Example 18 is the wearable ultrasound device of example 1 that may optionally include that the display device is implemented to display guidance for a procedure at the procedure site.

Example 19 is an operator-worn ultrasound device comprising: an ultrasound transducer configured to transmit ultrasound signals at a patient anatomy and receive reflected ultrasound from the patient anatomy; a fastener configured to secure the operator-worn ultrasound device to an operator of the operator-worn ultrasound device while permitting the operator to, with one hand, grip a patient and operate the ultrasound transducer; and a processor configured to generate, based on the reflected ultrasound, a visual representation that describes the patient anatomy.

Example 20 is a patient-worn ultrasound device comprising: an ultrasound transducer configured to transmit ultrasound signals at a patient anatomy and receive reflected ultrasound from the patient anatomy; a fastener configured to secure the patient-worn ultrasound device to a patient while permitting the patient to operate the ultrasound transducer with one hand and adjust a display device with the other hand; and a processor configured to generate, based on the reflected ultrasound, a visual representation that describes the patient anatomy.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in some embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A wearable ultrasound device comprising:

an array of ultrasound transducers configured to transmit ultrasound signals and receive reflected ultrasound based on the ultrasound signals;

a fastener coupled to the array of ultrasound transducers and configured to secure the wearable ultrasound device proximate to a procedure site, the fastener comprising a first section and a second section;

a blood pressure device on the first section of the fastener;

a processor configured to generate, based on the reflected ultrasound, patient data to determine an amount of compression to apply based on the patient data, wherein the processor is implemented to control a pressure of the blood pressure device when performing a blood pressure measurement by controlling inflation of the blood pressure device to achieve the amount of compression determined based on the patient data; and a display device implemented to display a visual representation of the patient data, wherein the array of ultrasound transducers is on the fastener to face a patient body part, and wherein the display device is on the fastener above at least a portion of the array of ultrasound transducers, wherein the display device is on the second section of the fastener, wherein the first section is above the procedure site and the second section is proximate to the procedure site.

2. The wearable ultrasound device as described in claim 1, wherein the fastener is implemented to secure the wearable ultrasound device to the patient body part that is proximate to the procedure site.

3. The wearable ultrasound device as described in claim 1, wherein the display device is implemented to display the visual representation without displaying an ultrasound image.

4. The wearable ultrasound device as described in claim 1, further comprising a marker source implemented to generate a marker and place the marker on a patient to indicate the procedure site.

5. The wearable ultrasound device as described in claim 4, wherein the marker source is implemented to generate the marker with at least one of ink and light.

6. The wearable ultrasound device as described in claim 4, wherein the marker indicates an insertion point for an interventional instrument.

7. The wearable ultrasound device as described in claim 4, wherein the processor is implemented to determine a surgical margin, and the marker indicates the surgical margin.

8. The wearable ultrasound device as described in claim 1, wherein the procedure site corresponds to a peripheral intravenous insertion, and the patient data includes a flow rate of fluid delivered by the peripheral intravenous insertion.

9. The wearable ultrasound device as described in claim 1, wherein the patient data indicates at least one of a medication ingestion and an activation of an ingested medication.

10. The wearable ultrasound device as described in claim 1, further comprising a heat source implemented to direct heat at an anatomy of the procedure site.

11. The wearable ultrasound device as described in claim 1, further comprising a pressure device implemented to apply pressure to a blood vessel for cannulation of the blood vessel at the procedure site.

12. The wearable ultrasound device as described in claim 1, wherein the fastener is implemented to remove the wearable ultrasound device from proximity of the procedure site prior to a procedure being performed at the procedure site.

13. The wearable ultrasound device as described in claim 1, wherein the array of ultrasound transducers is implemented to transmit the ultrasound signals and receive the reflected ultrasound concurrently with a procedure performed at the procedure site.

14. The wearable ultrasound device as described in claim 1, further comprising a guide for an interventional instrument for insertion at the procedure site.

15. The wearable ultrasound device as described in claim 1, wherein the patient data includes at least one of blood pressure data, a compression of a blood vessel, a blood vessel patency, a blood flow rate, and an indication of tissue repair.

16. The wearable ultrasound device as described in claim 1, wherein the display device is implemented to display guidance for a procedure at the procedure site.

17. An operator-worn ultrasound device comprising:

an array of ultrasound transducers configured to transmit ultrasound signals at a patient anatomy and receive reflected ultrasound from the patient anatomy;

a fastener configured to secure the operator-worn ultrasound device to one hand of an operator of the operator-worn ultrasound device while permitting the operator to, with the one hand, grip a patient and operate the ultrasound transducer, the array of ultrasound transducers being located at a bottom of the fastener that is on a first side of the one hand and in contact with the patient to transmit the ultrasound signals and receive the reflected ultrasound from the patient anatomy while the one hand grips the patient;

a display device on a top of the fastener that is on a second side of the one hand opposite the first side; and a processor configured to generate, based on the reflected ultrasound, a visual representation that includes guidance for a procedure for the patient anatomy and display the visual representation on the display device.

18. A patient-worn ultrasound device comprising:

an array of ultrasound transducers configured to transmit ultrasound signals at a patient anatomy and receive reflected ultrasound from the patient anatomy;

a display device coupled to the array of ultrasound transducers;

a fastener including a first section and a second section adjacent to the first section that is configured to secure the patient-worn ultrasound device to a patient while permitting the patient to operate the array of ultrasound transducers with one hand and adjust the display device with the other hand;

a blood pressure device on the first section of the fastener, wherein the display device is on the second section of the fastener, wherein the first section is above the procedure site and the second section is proximate to the procedure site; and a processor configured to generate, based on the reflected ultrasound, a visual representation that describes the patient anatomy, wherein the processor is implemented to control a pressure of the blood pressure device based on the reflected ultrasound by controlling inflation of the blood pressure device when performing a blood pressure measurement to achieve an amount of compression determined from the patient data generated from the reflected ultrasound.

* * * * *